US012746382B2

(12) United States Patent
Gloeckner et al.

(10) Patent No.: US 12,746,382 B2
(45) Date of Patent: Sep. 29, 2026

(54) BALLOON BLOCKER FOR OCCLUSION AND SUCTION

(71) Applicant: C. R. Bard, Inc., Franklin Lakes, NJ (US)

(72) Inventors: D. Claire Gloeckner, Lilburn, GA (US); Jill Walthall Jones, Avondale Estates, GA (US); Dinesh Puppala, San Bruno, CA (US); Patrick Hudson Chancy, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1011 days.

(21) Appl. No.: 17/873,923

(22) Filed: Jul. 26, 2022

(65) Prior Publication Data

US 2023/0030637 A1 Feb. 2, 2023

Related U.S. Application Data

(60) Provisional application No. 63/227,764, filed on Jul. 30, 2021.

(51) Int. Cl.
*A61M 39/22* (2006.01)
*A61M 25/00* (2006.01)

(52) U.S. Cl.
CPC ...... *A61M 39/227* (2013.01); *A61M 25/0017* (2013.01); *A61M 2205/7536* (2013.01)

(58) Field of Classification Search
CPC ............ A61M 39/227; A61M 25/0017; A61M 2205/7536

(Continued)

(56) References Cited

U.S. PATENT DOCUMENTS 3,114,916 A 12/1963 Hadley
3,583,401 A 6/1971 Vailiancourt et al.
(Continued)

FOREIGN PATENT DOCUMENTS

CN 106955208 A 7/2017
CN 116650740 A 8/2023
(Continued)

OTHER PUBLICATIONS

PCT/US2020/066707 filed Dec. 22, 2020 International Search Report and Written Opinion dated Apr. 15, 2021.

(Continued)

*Primary Examiner* — Phillip A Gray
(74) *Attorney, Agent, or Firm* — Rutan & Tucker LLP

(57) ABSTRACT

Embodiments disclosed herein are directed to a drainage system for draining a fluid from a patient where the system includes a drainage tube that provides fluid communication between a catheter and a collection container. The drainage tube includes a port and a balloon attached to an interior of the drainage tube, where the balloon is configured to receive air from a needle that has pierced the port and occlude a lumen of the drainage tube. When in an inflated state, the balloon occludes the lumen of the drainage tube thereby breaking the fluid communication between the catheter and the collection container and preventing the output airflow device from drawing airflow out of the catheter. The balloon may be attached to the interior of the drainage tube by surrounding an interior side of the port.

14 Claims, 7 Drawing Sheets

(58) Field of Classification Search
USPC .......................................................... 604/103
See application file for complete search history.

(56) References Cited

U.S. PATENT DOCUMENTS 3,598,124 A 8/1971 Andersen et al.
3,661,143 A 5/1972 Henkin
3,707,972 A 1/1973 Villari et al.
3,861,394 A 1/1975 Villari
3,901,235 A 8/1975 Patel et al.
3,955,574 A 5/1976 Rubinstein
4,013,076 A 3/1977 Puderbaugh et al.
4,084,593 A 4/1978 Jarund
4,250,872 A 2/1981 Tamari
4,265,243 A 5/1981 Taylor
4,266,689 A 5/1981 Asher
4,305,403 A 12/1981 Dunn
4,315,506 A 2/1982 Kayser et al.
4,360,933 A 11/1982 Kimura et al.
4,465,485 A 8/1984 Kashmer et al.
4,490,144 A 12/1984 Steigerwald
4,531,939 A 7/1985 Izumi
4,556,997 A 12/1985 Takamiya et al.
4,631,061 A 12/1986 Martin
4,654,029 A 3/1987 D'Antonio
4,711,365 A 12/1987 Fomby
4,747,166 A 5/1988 Kuntz
4,810,242 A 3/1989 Sundblom et al.
4,819,684 A 4/1989 Zaugg et al.
4,872,579 A 10/1989 Palmer
4,880,411 A 11/1989 Fangrow, Jr. et al.
4,990,137 A 2/1991 Graham
5,002,528 A 3/1991 Palestrant
5,071,411 A 12/1991 Hillstead
5,100,376 A 3/1992 Blake, III
5,186,431 A 2/1993 Tamari
5,242,404 A 9/1993 Conley et al.
5,318,550 A 6/1994 Cermak et al.
5,359,233 A 10/1994 Mumper et al.
5,405,319 A 4/1995 Abell et al.
RE35,707 E 12/1997 Takamiya et al.
5,738,656 A 4/1998 Wagner et al.
5,813,842 A 9/1998 Tamari
5,894,608 A 4/1999 Birbara
6,007,521 A 12/1999 Bidwell et al.
6,106,506 A 8/2000 Abell et al.
6,183,454 B1 2/2001 Levine et al.
7,833,186 B1* 11/2010 Batiste ................ A61M 1/3655
604/9
8,266,741 B2 9/2012 Penninger et al.
8,337,475 B2 12/2012 Christensen et al.
8,366,692 B2 2/2013 Weston et al.
8,475,419 B2 7/2013 Eckermann
8,512,301 B2 8/2013 Ma
9,814,866 B1 11/2017 Goswami
10,363,184 B2 7/2019 Zerhusen et al.
10,391,275 B2 8/2019 Burnett et al.
10,426,919 B2 10/2019 Erbey, II et al.
10,506,965 B2 12/2019 Cooper et al.
10,737,057 B1 8/2020 Mikhail et al.
10,772,998 B2 9/2020 Luxon et al.
12,097,150 B2 9/2024 Chancy et al.
12,128,188 B2 10/2024 Cheng et al.
2002/0000253 A1 1/2002 Fillmore et al.
2002/0087131 A1 7/2002 Wolff et al.
2002/0161317 A1 10/2002 Risk et al.
2003/0078638 A1 4/2003 Voorhees et al.
2004/0176746 A1 9/2004 Forral
2004/0230181 A1 11/2004 Cawood
2004/0236292 A1 11/2004 Tazoe et al.
2004/0254547 A1 12/2004 Okabe et al.
2005/0183780 A1 8/2005 Michaels et al.
2005/0197647 A1 9/2005 Dolliver et al.
2005/0209585 A1 9/2005 Nord et al.
2005/0245898 A1 11/2005 Wright et al.
2005/0256460 A1 11/2005 Rome et al.
2005/0261619 A1 11/2005 Gay
2006/0015190 A1 1/2006 Robertson
2006/0079854 A1 4/2006 Kay et al.
2006/0155260 A1 7/2006 Blott et al.
2006/0213527 A1 9/2006 Argenta et al.
2006/0235353 A1 10/2006 Gelfand et al.
2006/0270971 A1 11/2006 Gelfand et al.
2006/0271019 A1 11/2006 Stoller et al.
2007/0005002 A1 1/2007 Millman et al.
2007/0078444 A1 4/2007 Larsson
2007/0142729 A1 6/2007 Pfeiffer et al.
2007/0272311 A1 11/2007 Trocki et al.
2008/0051708 A1 2/2008 Kumar et al.
2008/0156092 A1 7/2008 Boiarski
2008/0281254 A1 11/2008 Humayun et al.
2008/0312550 A1 12/2008 Nishtala et al.
2009/0076469 A1 3/2009 Alexandersen
2009/0157016 A1 6/2009 Adahan
2009/0157040 A1 6/2009 Jacobson et al.
2009/0326483 A1 12/2009 Green
2010/0042059 A1 2/2010 Pratt et al.
2010/0106116 A1 4/2010 Simmons et al.
2010/0130949 A1 5/2010 Garcia
2010/0280435 A1 11/2010 Raney et al.
2011/0060300 A1 3/2011 Weig et al.
2012/0036638 A1 2/2012 Penninger et al.
2012/0323144 A1 12/2012 Coston et al.
2013/0218106 A1 8/2013 Coston et al.
2014/0053841 A1 2/2014 Ratner
2014/0200558 A1 7/2014 McDaniel
2014/0200588 A1 7/2014 Anderson et al.
2014/0276497 A1 9/2014 Robinson et al.
2015/0126975 A1 5/2015 Wuthier
2015/0141957 A1 5/2015 Hauswald
2015/0290448 A1 10/2015 Pavlik
2016/0135982 A1 5/2016 Garcia
2016/0183819 A1 6/2016 Burnett et al.
2016/0310711 A1 10/2016 Luxon et al.
2017/0014560 A1 1/2017 Minskoff et al.
2017/0014617 A1 1/2017 Huici
2017/0072125 A1 3/2017 Wallenås et al.
2017/0136209 A1* 5/2017 Burnett ................... A61M 1/60
2017/0143566 A1 5/2017 Elku et al.
2017/0209630 A1 7/2017 Klusmann et al.
2017/0241978 A1 8/2017 Duval
2017/0312114 A1 11/2017 Glithero
2018/0015251 A1 1/2018 Lampotang et al.
2018/0071441 A1 3/2018 Croteau et al.
2018/0104391 A1 4/2018 Luxon et al.
2018/0110456 A1 4/2018 Cooper et al.
2018/0125697 A1 5/2018 Ferrera
2018/0177458 A1 6/2018 Burnett et al.
2018/0185222 A1 7/2018 Zerhusen et al.
2018/0235523 A1 8/2018 Sauder
2018/0245699 A1 8/2018 Lee
2018/0360424 A1 12/2018 Yurek et al.
2019/0009021 A1 1/2019 Nelson et al.
2019/0009023 A1 1/2019 Diperna et al.
2019/0030264 A1 1/2019 Herskovic et al.
2019/0038451 A1 2/2019 Harvie
2019/0046102 A1 2/2019 Kushnir et al.
2019/0126006 A1 5/2019 Rehm et al.
2019/0143008 A1 5/2019 Brundage et al.
2019/0143094 A1 5/2019 DeMeritt
2019/0151610 A1 5/2019 Fletter
2019/0175801 A1 6/2019 Levine
2019/0255242 A1* 8/2019 Cull .................... A61M 39/227
2019/0343445 A1 11/2019 Burnett et al.
2020/0000979 A1 1/2020 Myers
2020/0061281 A1 2/2020 Desouza et al.
2020/0155751 A1* 5/2020 Batiste ...................... A61F 2/06
2020/0315837 A1 10/2020 Radl et al.
2021/0077007 A1 3/2021 Jouret et al.
2022/0152345 A1 5/2022 Simiele et al.
2022/0160949 A1 5/2022 Simiele et al.
2022/0176031 A1 6/2022 Cheng et al.
2022/0193366 A1 6/2022 Cheng et al.
2022/0218890 A1 7/2022 Chavan

(56) References Cited

U.S. PATENT DOCUMENTS

| | | | |
|---|---|---|---|
| 2022/0218973 | A1 | 7/2022 | Chavan et al. |
| 2022/0218974 | A1 | 7/2022 | Chavan et al. |
| 2022/0273213 | A1 | 9/2022 | Sokolov et al. |
| 2022/0287689 | A1 | 9/2022 | Johannes |
| 2022/0305189 | A1 | 9/2022 | Chavan et al. |
| 2022/0330867 | A1 | 10/2022 | Conley et al. |
| 2022/0362080 | A1 | 11/2022 | McCorquodale et al. |
| 2022/0409421 | A1 | 12/2022 | Hughett et al. |
| 2023/0013353 | A1 | 1/2023 | Chavan et al. |
| 2023/0054937 | A1 | 2/2023 | Chancy et al. |
| 2023/0083906 | A1 | 3/2023 | Jones et al. |
| 2023/0277199 | A1 | 9/2023 | Duffy |
| 2023/0310837 | A1 | 10/2023 | Gamsizlar et al. |
| 2024/0033404 | A1 | 2/2024 | Ishikawa |
| 2024/0238500 | A1 | 7/2024 | Simiele et al. |
| 2024/0307604 | A1 | 9/2024 | Chavan |
| 2025/0009578 | A1 | 1/2025 | Chancy et al. |
| 2025/0018147 | A1 | 1/2025 | Rehm |
| 2025/0018149 | A1 | 1/2025 | Cheng et al. |
| 2025/0025617 | A1 | 1/2025 | Chavan et al. |
| 2025/0025620 | A1 | 1/2025 | Cheng et al. |
| 2025/0040848 | A1 | 2/2025 | Lai et al. |
| 2025/0177632 | A1 | 6/2025 | Jones et al. |
| 2025/0186735 | A1 | 6/2025 | Rehm et al. |
| 2025/0288775 | A1 | 9/2025 | Simiele et al. |
| 2026/0014310 | A1 | 1/2026 | Chavan |
| 2026/0108376 | A1 | 4/2026 | Chavan et al. |
| 2026/0199121 | A1 | 7/2026 | Khurana et al. |

FOREIGN PATENT DOCUMENTS

| | | | |
|---|---|---|---|
| EP | 1122435 | A1 | 8/2001 |
| EP | 1872752 | A1 | 1/2008 |
| EP | 2417955 | A2 | 2/2012 |
| EP | 2730299 | A1 | 5/2014 |
| EP | 4096611 | B1 | 5/2025 |
| EP | 4585150 | A2 | 7/2025 |
| GB | 1408821 | A | 10/1975 |
| GB | 2235256 | | 2/1991 |
| WO | 2009/026237 | A1 | 2/2009 |
| WO | 2012016179 | A1 | 2/2012 |
| WO | 2015019056 | A1 | 2/2015 |
| WO | 2015/105916 | A1 | 7/2015 |
| WO | 2016012494 | A1 | 1/2016 |
| WO | 2017177068 | A1 | 10/2017 |
| WO | 2018136306 | A1 | 7/2018 |
| WO | 2018191193 | A1 | 10/2018 |
| WO | 2019004854 | A1 | 1/2019 |
| WO | 2019083104 | A1 | 5/2019 |
| WO | 2020/033752 | A1 | 2/2020 |
| WO | 2021154427 | A1 | 8/2021 |
| WO | 2021158332 | A1 | 8/2021 |
| WO | 2022108589 | A1 | 5/2022 |
| WO | 2022/159333 | A1 | 7/2022 |
| WO | 2022/251425 | A1 | 12/2022 |
| WO | 2023086394 | A1 | 5/2023 |
| WO | 2024118072 | A1 | 6/2024 |
| WO | 2024151250 | A1 | 7/2024 |
| WO | 2024162961 | A1 | 8/2024 |

OTHER PUBLICATIONS

PCT/US2022/012373 filed Jan. 13, 2022 International Search Report and Written Opinion dated Apr. 19, 2022.

U.S. Appl. No. 17/373,568, filed Jul. 12, 2021 Non-Final Office Action dated Nov. 9, 2023.

U.S. Appl. No. 17/526,994, filed Nov. 15, 2021 Advisory Action dated Jan. 19, 2024.

U.S. Appl. No. 17/526,994, filed Nov. 15, 2021 Final Office Action dated Oct. 24, 2023.

U.S. Appl. No. 17/532,454, filed Nov. 22, 2021 Final Office Action dated Sep. 27, 2023.

U.S. Appl. No. 17/532,454, filed Nov. 22, 2021 Notice of Allowance dated Dec. 8, 2023.

U.S. Appl. No. 17/542,060, filed Dec. 3, 2021 Non-Final Office Action dated Nov. 28, 2023.

U.S. Appl. No. 17/556,942, filed Dec. 20, 2021 Non-Final Office Action dated Nov. 3, 2023.

U.S. Appl. No. 17/561,458, filed Dec. 23, 2021 Notice of Allowance dated Dec. 6, 2023.

U.S. Appl. No. 17/561,504, filed Dec. 23, 2021 Non-Final Office Action dated Nov. 27, 2023.

U.S. Appl. No. 17/561,504, filed Dec. 23, 2021 Notice of Allowance dated Jan. 22, 2024.

U.S. Appl. No. 17/863,898, filed Jul. 13, 2022 Advisory Action dated Jan. 30, 2024.

U.S. Appl. No. 17/863,898, filed Jul. 13, 2022 Final Office Action dated Nov. 22, 2023.

U.S. Appl. No. 17/902,705, filed Sep. 2, 2022 Advisory Action dated Oct. 19, 2023.

U.S. Appl. No. 17/902,705, filed Sep. 2, 2022 Non-Final Office Action dated Dec. 7, 2023.

U.S. Appl. No. 17/526,994, filed Nov. 15, 2021 Non-Final Office Action dated May 10, 2023.

U.S. Appl. No. 17/532,454, filed Nov. 22, 2021 Non-Final Office Action dated Mar. 22, 2023.

U.S. Appl. No. 17/561,504, filed Dec. 23, 2021 Non-Final Office Action dated Mar. 14, 2023.

U.S. Appl. No. 17/902,705, filed Sep. 2, 2022 Non-Final Office Action dated May 24, 2023.

U.S. Appl. No. 17/526,994, filed Nov. 15, 2021 Final Office Action dated Nov. 19, 2024.

U.S. Appl. No. 17/526,994, filed Nov. 15, 2021 Notice of Allowance dated Feb. 5, 2025.

U.S. Appl. No. 17/571,254, filed Jan. 7, 2022 Non-Final Office Action dated Feb. 13, 2025.

U.S. Appl. No. 17/571,254, filed Jan. 7, 2022 Restriction Requirement dated Oct. 4, 2024.

U.S. Appl. No. 17/863,898, filed Jul. 13, 2022 Advisory Action dated Oct. 28, 2024.

U.S. Appl. No. 17/863,898, filed Jul. 13, 2022 Final Office Action dated Aug. 22, 2024.

U.S. Appl. No. 17/863,898, filed Jul. 13, 2022 Non-Final Office Action dated Dec. 2, 2024.

U.S. Appl. No. 17/902,705, filed Sep. 2, 2022 Advisory Action dated Aug. 1, 2024.

U.S. Appl. No. 17/902,705, filed Sep. 2, 2022 Notice of Allowance dated Sep. 18, 2024.

U.S. Appl. No. 18/274,157, filed Jul. 25, 2023 Non-Final Office Action dated Jan. 17, 2025.

U.S. Appl. No. 18/674,694, filed May 24, 2024 Non-Final Office Action dated Mar. 3, 2025.

PCT/US2022/049418 filed Nov. 9, 2022 International Search Report and Written Opinion dated Feb. 10, 2023.

U.S. Appl. No. 17/526,994, filed Nov. 15, 2021 Restriction Requirement dated Jan. 3, 2023.

U.S. Appl. No. 17/556,942, filed Dec. 20, 2021 Non-Final Office Action dated Jan. 31, 2023.

U.S. Appl. No. 17/542,060, filed Dec. 3, 2021 Non-Final Office Action dated Jun. 27, 2023.

U.S. Appl. No. 17/556,942, filed Dec. 20, 2021 Advisory Action dated Sep. 1, 2023.

U.S. Appl. No. 17/556,942, filed Dec. 20, 2021 Final Office Action dated Jul. 12, 2023.

U.S. Appl. No. 17/561,458, filed Dec. 23, 2021 Final Office Action dated Sep. 12, 2023.

U.S. Appl. No. 17/561,458, filed Dec. 23, 2021 Non-Final Office Action dated Jun. 16, 2023.

U.S. Appl. No. 17/561,504, filed Dec. 23, 2021 Final Office Action dated Jul. 19, 2023.

U.S. Appl. No. 17/863,898, filed Jul. 13, 2022 Non-Final Office Action dated Jul. 17, 2023.

U.S. Appl. No. 17/902,705, filed Sep. 2, 2022 Final Office Action dated Aug. 17, 2023.

(56) References Cited

OTHER PUBLICATIONS

U.S. Appl. No. 17/373,568, filed Jul. 12, 2021 Notice of Allowance dated Apr. 26, 2024.
U.S. Appl. No. 17/526,994, filed Nov. 15, 2021 Non-Final Office Action dated Apr. 22, 2024.
U.S. Appl. No. 17/542,060, filed Dec. 3, 2021 Notice of Allowance dated Jun. 3, 2024.
U.S. Appl. No. 17/556,942, filed Dec. 20, 2021 Final Office Action dated Apr. 4, 2024.
U.S. Appl. No. 17/556,942, filed Dec. 20, 2021 Notice of Allowance dated Jun. 26, 2024.
U.S. Appl. No. 17/796,604, filed Jul. 29, 2022 Notice of Allowance dated May 1, 2024.
U.S. Appl. No. 17/863,898, filed Jul. 13, 2022 Non-Final Office Action dated Mar. 11, 2024.
U.S. Appl. No. 17/902,705, filed Sep. 2, 2022 Final Office Action dated May 22, 2024.
EP 25167903.1 filed Apr. 2, 2025 Extended European Search Report dated Oct. 7, 2025.
PCT/US2022/051431 filed Nov. 30, 2022 International Search Report and Written Opinion dated May 22, 2022.
PCT/US2023/010515 filed Jan. 10, 2023 International Search Report and Written Opinion dated Sep. 12, 2023.
PCT/US2023/012095 filed Feb. 1, 2023 International Preliminary Report on Patentability dated Jul. 31, 2025.
PCT/US2023/012095 filed Feb. 1, 2023 International Search Report and Written Opinion dated Jul. 17, 2023.
U.S. Appl. No. 17/571,254, filed Jan. 7, 2022 Final Office Action dated Aug. 13, 2025.
U.S. Appl. No. 17/863,898, filed Jul. 13, 2022 Advisory Action dated Aug. 6, 2025.
U.S. Appl. No. 17/863,898, filed Jul. 13, 2022 Notice of Allowance dated Sep. 16, 2025.
U.S. Appl. No. 18/274,157, filed Jul. 25, 2023 Non-Final Office Action dated Sep. 19, 2025.
U.S. Appl. No. 18/622,604, filed Mar. 29, 2024 Non-Final Office Action dated Oct. 2, 2025.
U.S. Appl. No. 18/882,228, filed Sep. 11, 2024 Non-Final Office Action dated Oct. 1, 2025.
U.S. Appl. No. 18/899,727, filed Sep. 27, 2024 Notice of Allowance dated Sep. 30, 2025.
U.S. Appl. No. 17/701,395, filed Mar. 22, 2022 Non-Final Office Action dated Jun. 3, 2025.
U.S. Appl. No. 17/863,898, filed Jul. 13, 2022 Final Office Action dated Jun. 3, 2025.
U.S. Appl. No. 18/274,157, filed Jul. 25, 2023 Advisory Action dated Jul. 16, 2025.
U.S. Appl. No. 18/274,157, filed Jul. 25, 2023 Final Office Action dated May 5, 2025.
U.S. Appl. No. 18/674,694, filed May 24, 2024 Notice of Allowance dated Jun. 23, 2025.
U.S. Appl. No. 17/571,254, filed Jan. 7, 2022 Non-Final Office Action dated Mar. 25, 2026.
U.S. Appl. No. 17/701,395, filed Mar. 22, 2022 Advisory Action dated Feb. 19, 2026.
U.S. Appl. No. 17/701,395, filed Mar. 22, 2022 Final Office Action dated Dec. 17, 2025.
U.S. Appl. No. 17/701,395, filed Mar. 22, 2022 Notice of Allowance dated Apr. 15, 2026.
U.S. Appl. No. 18/274,157, filed Jul. 25, 2023 Final Office Action dated Jan. 6, 2026.
U.S. Appl. No. 18/274,157, filed Jul. 25, 2023 Notice of Allowance dated Mar. 30, 2026.
U.S. Appl. No. 18/622,604, filed Mar. 29, 2024 Final Office Action dated Apr. 7, 2026.
U.S. Appl. No. 18/706,737, filed May 1, 2024 Non-Final Office Action dated Mar. 13, 2026.
U.S. Appl. No. 18/882,228, filed Sep. 11, 2024 Notice of Allowance dated Feb. 5, 2026.
U.S. Appl. No. 18/899,727, filed Sep. 27, 2024 Notice of Allowance dated Mar. 19, 2026.
U.S. Appl. No. 18/706,737, filed May 1, 2024 Final Office Action dated Jul. 14, 2026.
U.S. Appl. No. 18/900,119, filed Sep. 27, 2024 Non-Final Office Action dated Jul. 21, 2026.

* cited by examiner

BALLOON BLOCKER FOR OCCLUSION AND SUCTION

PRIORITY

This application claims the benefit of priority to U.S. Provisional Application No. 63/227,764, filed Jul. 30, 2021, which is incorporated by reference in its entirety into this application.

BACKGROUND

Fluid drainage systems, often used with urinary catheterization, include a flexible drainage tube providing fluid communication with a collection container. The flexibility of the drainage tube can form sections of positive incline, also termed "dependent loops," where drainage fluid can accumulate. Fluid pooling within dependent loops can cause various complications. For example, urine pooling can be a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications.

Thus, what is needed are systems and methods for clearing drainage fluid from portions of the drainage tube, specifically from dependent loops.

SUMMARY OF THE INVENTION

Briefly summarized, disclosed herein are embodiments directed to systems and methods for clearing drainage fluid from dependent loops of a fluid drainage system. An embodiment of the drainage system includes a catheter, a collection container, a drainage tube configured to provide fluid communication between the catheter and the collection container, wherein the drainage tube includes a port and a balloon attached to an interior of the drainage tube, wherein an interior cavity of the balloon is configured to receive a gas from a needle that has pierced the port and occlude a lumen of the drainage tube, and an output airflow device coupled to the collection container configured to draw airflow out of the drainage tube.

When in an inflated state, the balloon occludes the lumen of the drainage tube thereby breaking the fluid communication between the catheter and the collection container and preventing the output airflow device from drawing airflow out of the catheter. In some embodiment, the balloon is attached to the interior of the drainage tube by surrounding an interior side of the port. The port may include a self-sealing membrane and may be located at a distal end of the drainage tube. The system may further include a hydrophobic filter coupled in line with the drainage tube between the collection container and the output airflow device.

Another embodiment of the disclosure includes a method of draining fluid from a patient. The method including steps of providing a drainage system comprising a catheter, a collection container, a drainage tube configured to provide fluid communication between the catheter and the collection container, wherein the drainage tube includes a port and a balloon attached to an interior of the drainage tube, an output airflow device coupled to the collection container, inflating the balloon thereby occluding a lumen of the drainage tube, and activating the output airflow device to withdraw airflow out of the drainage tube. Inflating the balloon may include piercing a membrane of the port with a needle of a syringe thereby inserting the needle into an interior cavity of the balloon and compressing the syringe thereby inserting gas into the balloon.

Another embodiment of the disclosure includes a drainage tube for use within a drainage system for draining a fluid from a patient, the drainage system including a catheter, a collection container and an output airflow device coupled to the collection container, the drainage tube comprising a tubing having a lumen extending from a proximal end to a distal end, a port, and a balloon attached to an interior of the drainage tube, wherein an interior cavity of the balloon is configured to receive a gas from a needle that has pierced the port, and occlude a lumen of the drainage tube.

Yet another embodiment of the disclosure is directed to a drainage system for draining a fluid from a patient comprises a catheter, a collection container, a drainage tube in fluid communication with the collection container, an output airflow device coupled to the collection container configured to draw airflow out of the drainage tube, and a connector tube configured to provide fluid communication between the catheter and the drainage tubing, wherein the connector tube includes a port and a balloon attached to an interior of the connector tube, wherein an interior cavity of the balloon is configured to receive a gas from a needle that has pierced the port, and occlude a lumen of the connector tube.

When in an inflated state, the balloon occludes the lumen of the connector tube thereby breaking the fluid communication between the catheter and the collection container and preventing the output airflow device from drawing airflow out of the catheter. The balloon may be attached to the interior of the connector tube by surrounding an interior side of the port. The port may include a self-sealing membrane. The system may include a hydrophobic filter coupled in line with the connector tube between the collection container and the output airflow device.

Still yet another embodiment of the disclosure is directed to a method of draining fluid from a patient including steps of providing a drainage system comprising a catheter, a collection container, a drainage tube in fluid communication with the collection container, an output airflow device coupled to the collection container configured to draw airflow out of the drainage tube, and a connector tube configured to provide fluid communication between the catheter and the drainage tubing, wherein the connector tube includes a port and a balloon attached to an interior of the connector tube, wherein an interior cavity of the balloon is configured to receive a gas from a needle that has pierced the port, and occlude a lumen of the connector tube, inflating the balloon thereby occluding a lumen of the connector tube and activating the output airflow device to withdraw airflow out of the drainage tube.

Inflating the balloon may include piercing a membrane of the port with a needle of a syringe thereby inserting the needle into an interior cavity of the balloon and compressing the syringe thereby inserting gas into the balloon. When in an inflated state, the balloon occludes the lumen of the connector tube thereby breaking the fluid communication between the catheter and the collection container and preventing the output airflow device from drawing the airflow out of the catheter. The balloon may be attached to the interior of the connector tube by surrounding an interior side of the port. The port may include a self-sealing membrane. The drainage system may include a hydrophobic filter coupled in line with the connector tube between the collection container and the output airflow device.

These and other features of the concepts provided herein will become more apparent to those of skill in the art in view of the accompanying drawings and the following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
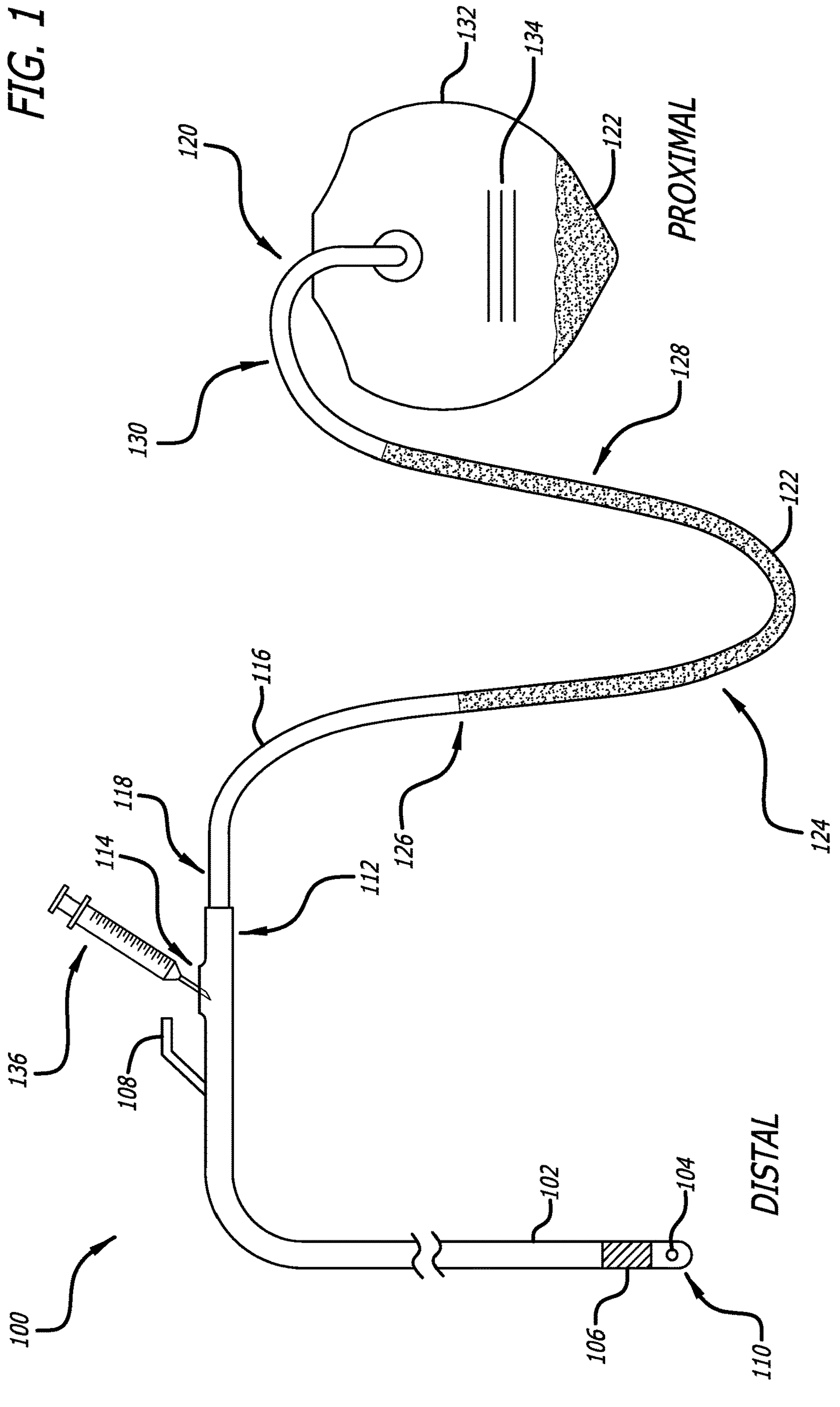
FIG. 1 shows a catheter and fluid collection system including a dependent loop, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

The phrases "connected to" and "coupled to" refer to any form of interaction between two or more entities, including mechanical, electrical, magnetic, electromagnetic, fluid, signal, communicative, operative, and thermal interaction. Two components may be connected or coupled to each other even though they are not in direct contact with each other. For example, two components may be coupled to each other through an intermediate component.

The phrase "to exceed" means to go beyond. For example, a parameter may exceed an upper parameter limit by going above the upper parameter limit or exceed a lower parameter limit by going below the lower parameter limit. Similarly, a parameter may exceed a positive limit by going more positive than the positive limit or the parameter may exceed a negative limit by going more negative than the negative limit.

FIG. 1 shows a catheter and fluid collection system ("system") 100, which includes a catheter 102, a drainage tube 116 and a collection container ("container") 132. Exemplary catheters 102 include indwelling catheters, Foley catheters, balloon catheters, peritoneal drainage catheters, or the like, and are configured to be inserted into an orifice within the body of a patient to drain a fluid therefrom. In an embodiment, the catheter 102 can be inserted through the urethra and into a bladder of a patient. The catheter 102 includes an eyelet 104 that provides fluid communication with a lumen of the catheter 102, and is configured to drain a fluid, e.g. urine, and further includes an inflatable balloon 106 at the distal end 110. The catheter 102 may further include a balloon port 108 through which the balloon 106 is inflated/deflated and a sampling port 114 at a proximal end. A syringe may be utilized to extract liquid from the system 100 via the sampling port 114. The catheter 102 extends from the proximal end 112 to the distal end 110.

The drainage tube 116 extends from a distal end 118 to a proximal end 120 to define an axial length, and defines a lumen 124 therein. When the catheter 102 and the drainage tube 116 are coupled (as shown), fluid communication is established between the two components at the distal end 118 of the drainage tube 116 and the proximal end 112 of the catheter 102. The drainage tube 116 provides fluid communication between the lumen of the catheter 102 and the collection container 132. The drainage tube 116 can be formed of rubber, plastic, polymer, silicone, or similar suitable material. The collection container 132 can include a rigid container, a flexible collection bag, or similar suitable container for receiving a fluid, e.g. urine, drained from the catheter 102. In operation, the drainage system 100 may facilitate a passive draining process of liquid 122 from the patient without incident. However, in some instances, one or more complications may arise during the passive draining process requiring corrective action.

Figure 2B:
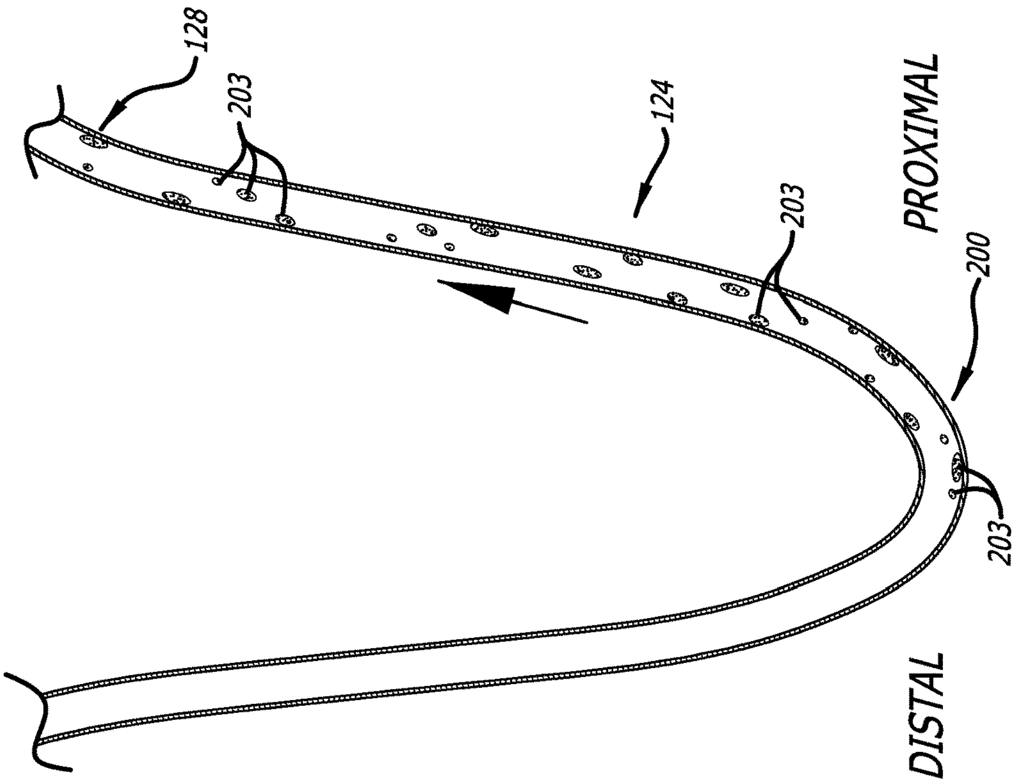
FIG. 2B illustrates fluid droplets within a dependent loop, in accordance with embodiments disclosed herein.
Figure 2A:
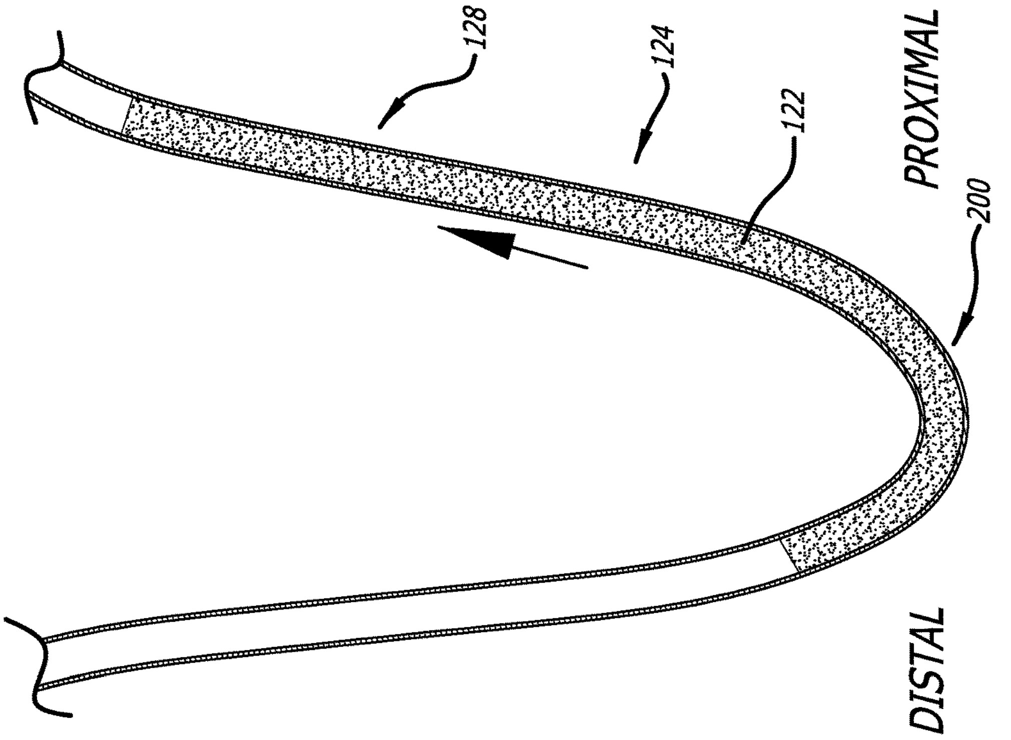
FIG. 2A illustrates a column of liquid within a dependent loop, in accordance with embodiments disclosed herein.

Specifically, as shown in FIG. 1, a dependent loop 124 is shown within the drainage tube 116 with liquid 122 collected therein. Due to the dependent loop 124, the liquid 122 may remain in stagnant at least due to the include 128 and fail to reach the collection bag 132. As noted above, this stagnant liquid (e.g., urine pooling) can be a source of catheter-associated urinary tract infection ("CAUTI") causing agents such as bacteria, microbes, and the like, which are detrimental to the patient FIGS. 2A-2B illustrate a segment of the dependent loop 124 of the drainage tube 116 including a trough 210 and the incline 120. The liquid 122 disposed within the drainage tube 116 can form a liquid column 223 (FIG. 2A) or liquid droplets 203 (FIG. 2B). As shown in FIG. 2A, the liquid column 223 may extend from a distal side of the trough 210 to a proximal side of the trough 210. The liquid column 223 extends across the entire cross-sectional area of the drainage lumen 130. When the liquid 122 is in the form of the column 223, an internal air pressure of the drainage tube 116 distal of the column 223 may urge the column 223 proximally along the drainage tube 116. The pressure needed to move the column 223 up the incline 120 of the tubing 120 may be at least partially defined by a height of the liquid column 223.

FIG. 2B shows the liquid 122 in the form of droplets 203 disposed along the incline 120 of the drainage tube 116. The column 223 may generally break up into the droplets 203 when a distal end of the column 223 is disposed on the proximal side of the trough 210. When the liquid 122 is in the form of droplets 203, airflow may flow around the droplets 203. As such, the internal air pressure may not urge the liquid 122 in the form of droplets 203 proximally along the drainage tube 116. In this scenario, proximal displacement of the droplets 203 may rely on proximally oriented drag forces on the droplets 203 defined by an airflow rate rather than an internal pressure. The drag force is a function of the dynamic pressure of the airflow and the dynamic pressure is proportional to the airflow rate squared. As such, the airflow required to proximally urge to the droplets 203 along the drainage tube 116 may be greater than the airflow required to proximally urge to the column 223 along the drainage tube 116.

Figure 3A:
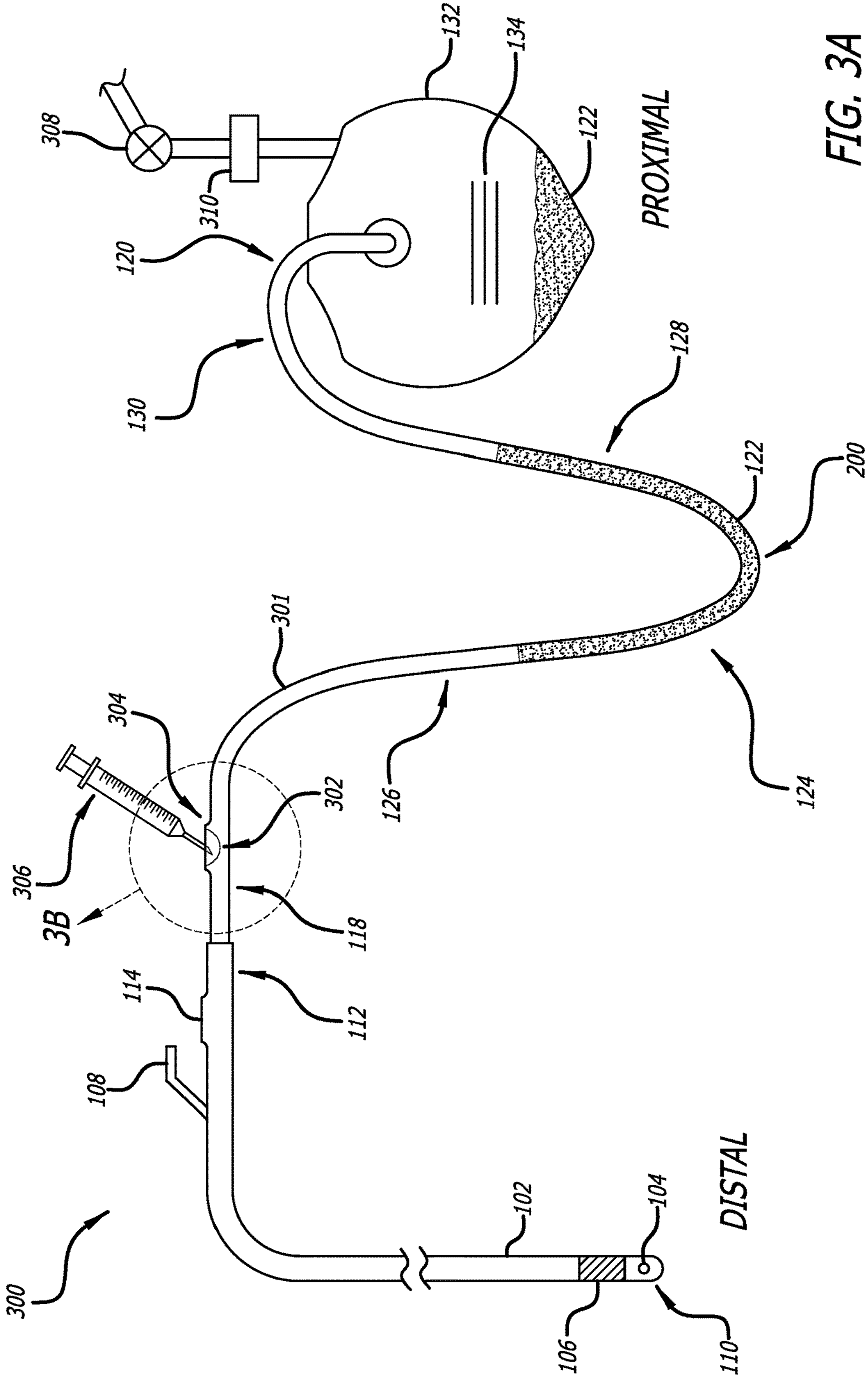
FIG. 3A shows a first catheter and fluid collection system including a drainage tube having an occlusion balloon port with an occlusion balloon in a deflated state, in accordance with embodiments disclosed herein.

FIG. 3A shows a first catheter and fluid collection system including a drainage tube having an occlusion balloon port with an occlusion balloon in a deflated state, in accordance with embodiments disclosed herein. It will be appreciated that the system illustrated in FIGS. 3A-3B may have analogous features to the system 100 of FIG. 1. Accordingly, like features are designated with like reference numerals. Relevant disclosure set forth above regarding similarly identified features thus may not be repeated hereafter. Moreover, specific features of the system 100 and related components shown in FIGS. 1-2B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 100 or portions thereof illustrated in FIGS. 1-2B. Any suitable combination of the features, and variations of the same, described with respect to the systems and components described herein and illustrated in any of the accompanying drawings can be employed with the systems 100, 300. This pattern of disclosure applies equally to further embodiments (e.g., system 400) depicted in subsequent figures and described hereafter. Additionally, all embodiments disclosed herein are combinable and/or interchangeable unless stated otherwise or such combination or interchange would be contrary to the stated operability of either embodiment.

The system 300 includes the catheter 102 coupled with drainage tubing 301 that extends from a distal end 118 to a proximal end 120 and is flexible in nature such that dependent loops (e.g., the dependent loop 200) may form from time to time along the length of the tubing 301. In contrast to the tubing 116 of FIG. 1, the tubing 301 includes a balloon occlusion port 304 and an occlusion balloon 302 attached to the port 304 and disposed within the lumen of the tubing 301. The port 304, shown in greater detail in FIG. 3B, may be similar to the port 114 and may include a self-sealing membrane that is configured to be pierced by a needle. The membrane may be formed of suitable materials such as Chlorobutyl or other synthetic or natural elastic polymers. In some embodiments, the membranes may be non-latex and TEFLON®-coated.

The balloon 302 may be a highly elastic balloon that is directed coupled to the interior of the tubing 301 such that an opening of the balloon 302 surrounds the membrane of the port 304. As a result, a clinician may pierce the membrane of the port 304 with a needle of the syringe 306 and enter the interior cavity of the balloon 302. The clinician may then inflate the balloon 302 by compressing the syringe 306 to force a gas (e.g., air) into the balloon 302, shown in FIG. 3C.

The system 300 also includes an output airflow device 308 coupled to the container 132 and/or to the drainage tube 301 at a proximal end 130 thereof. The output airflow device 308 may be coupled to the container 132 so that the airflow device 308 can draw air out of the container 132 while leaving the liquid 122 within the container 132 (e.g., act to suction air out of the container 132). More specifically, the output airflow device 308 may be coupled to the container 132 at an upper location of the container, i.e., above the liquid level within the container 132. In some embodiments, the output airflow device 308 may be an adjustable vacuum, i.e., capable of providing airflow at different rates. The output airflow device 308 may be continuously adjustable across a range of airflow rates or the output airflow device 308 may be discreetly adjustable across a plurality of discreet airflow rates.

In some embodiments, the system 300 may include a filter 310 disposed between the container 132 and the output airflow device 308. The filter 310 may be formed of a hydrophobic material. The filter 310 may allow airflow out of the container 132 and prevent liquid flow out of the container 132. By preventing liquid flow out of the container 132, the volume of drainage liquid may be accurately measured and the output airflow device 308 may be protected from liquid damage.

Figure 3B:
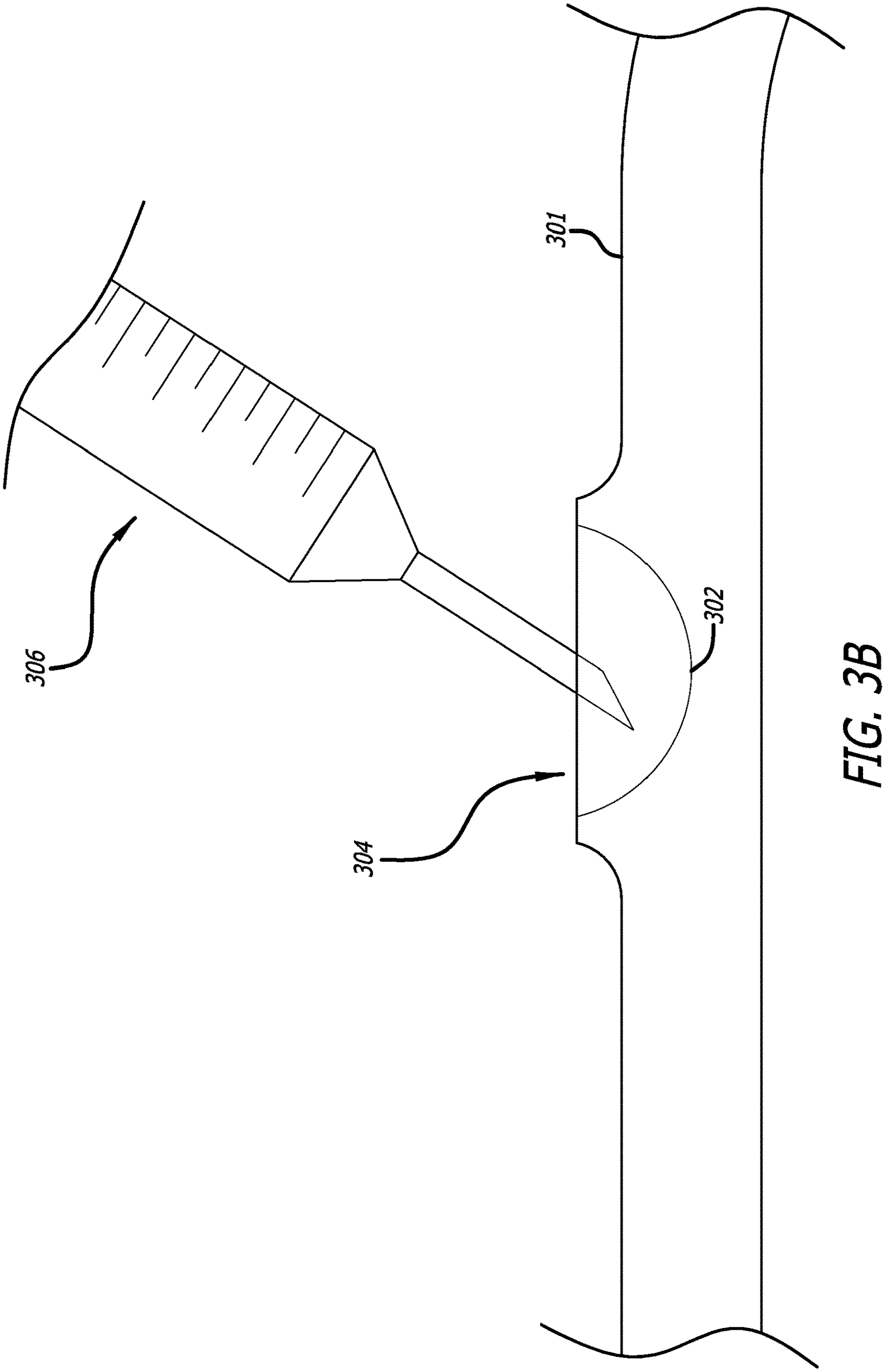
FIG. 3B shows a detailed view of a distal end of the draining tubing of the system of FIG. 3A including a balloon occlusion port, in accordance with some embodiments disclosed herein.

FIG. 3B shows a detailed cross-sectional view of a portion of the drainage tubing 301 of the system of FIG. 3A including a balloon occlusion port, in accordance with some embodiments. The balloon 302 is shown as attached to the interior of the tubing 301 surrounding the membrane of the port 304. As the needle of the syringe 306 pierces the membrane, the needle enters the interior cavity of the balloon 302. Upon compression of the syringe 306 by a clinician, air within the syringe enters the interior cavity of the balloon 302 and causes the balloon 302 to transition from a deflated state (FIGS. 3A-3B) to an inflated state (FIG. 3C).

Figure 3C:
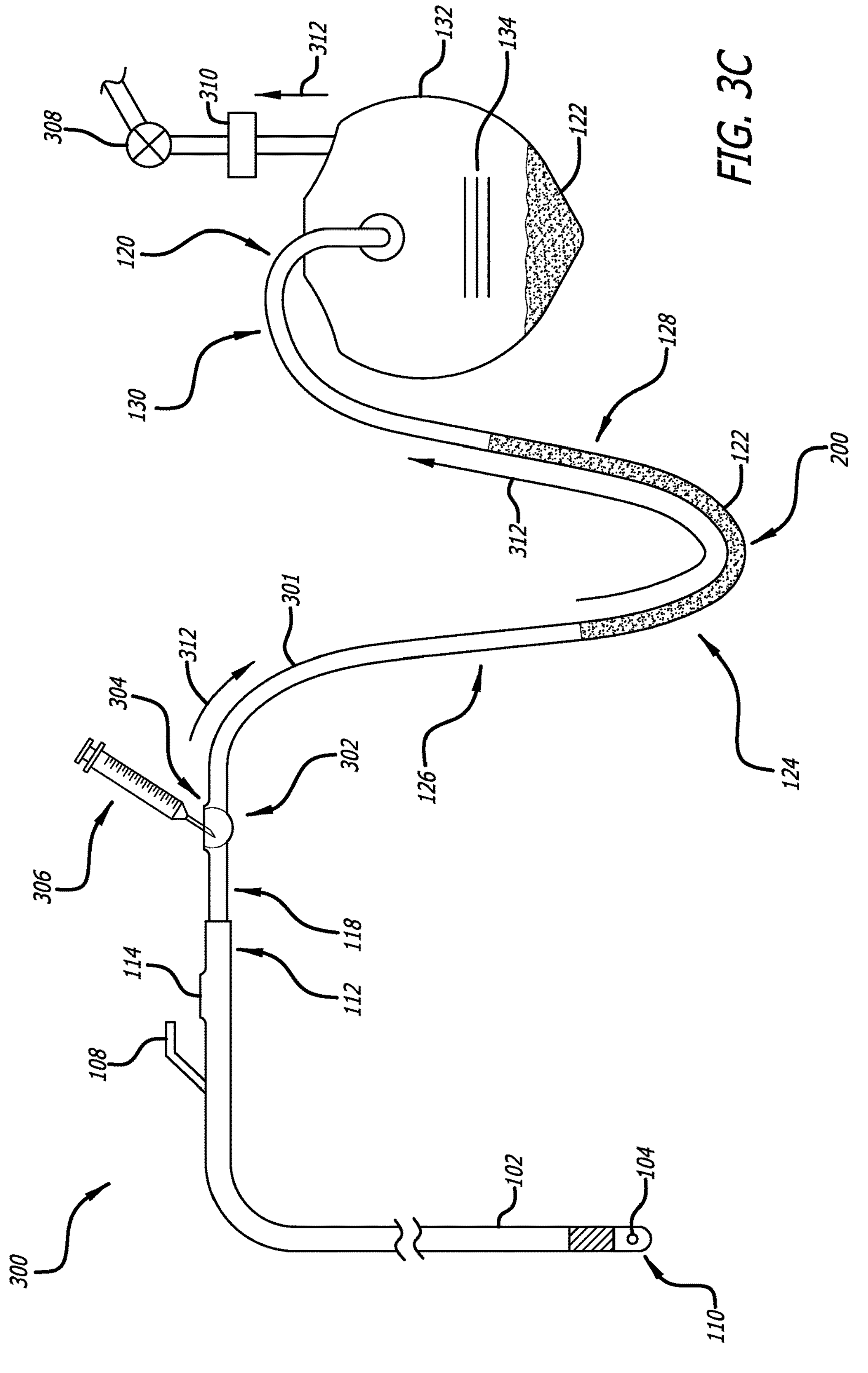
FIG. 3C shows the catheter and fluid collection system of FIG. 3A where the occlusion balloon is in an inflated state, in accordance with embodiments disclosed herein.

FIG. 3C shows the catheter and fluid collection system 300 of FIG. 3A where the occlusion balloon 302 is in an inflated state, in accordance with embodiments disclosed herein. When inflated, the balloon 302 occludes the lumen of the tubing 301. When in an inflated state, the balloon 302 breaks the fluid communication between the distal end 110 of the catheter 102 and the container 132. In some embodiments, the balloon 302 may be inflated to a degree that causes the tubing 301.

Following inflation of the balloon 302, the output airflow device 308 may be operated to draw air out of container 132 and the tubing 301. As a result, the liquid 122 is drawn from tubing 301 into the container 132. More specifically, the liquid 122 is drawn out of the dependent loop 200 in a flushing manner. As the inflated balloon 302 occludes the lumen of the tubing 301 at its distal end 118, the suction 312 does not reach catheter 102. Advantageously, the suction 312 does not draw air or liquid from a bladder of a patient in which the catheter 102 is disposed.

Operation of the output airflow device 308 may be ceased thereby removing the presence of the suction 312. Once the suction 312 has been terminated, the balloon 302 may be deflated by withdrawing the air back into the syringe and the needle may be removed from the port 304. As the balloon 302 surrounds the port 304, liquid 122 passing from the distal end 110 of the catheter 102 to the container 132 is not able to leak out through any puncture that may remain in the port 304. However, as the membrane of the port 304 is self-sealing, no such puncture should be present.

Figure 4A:
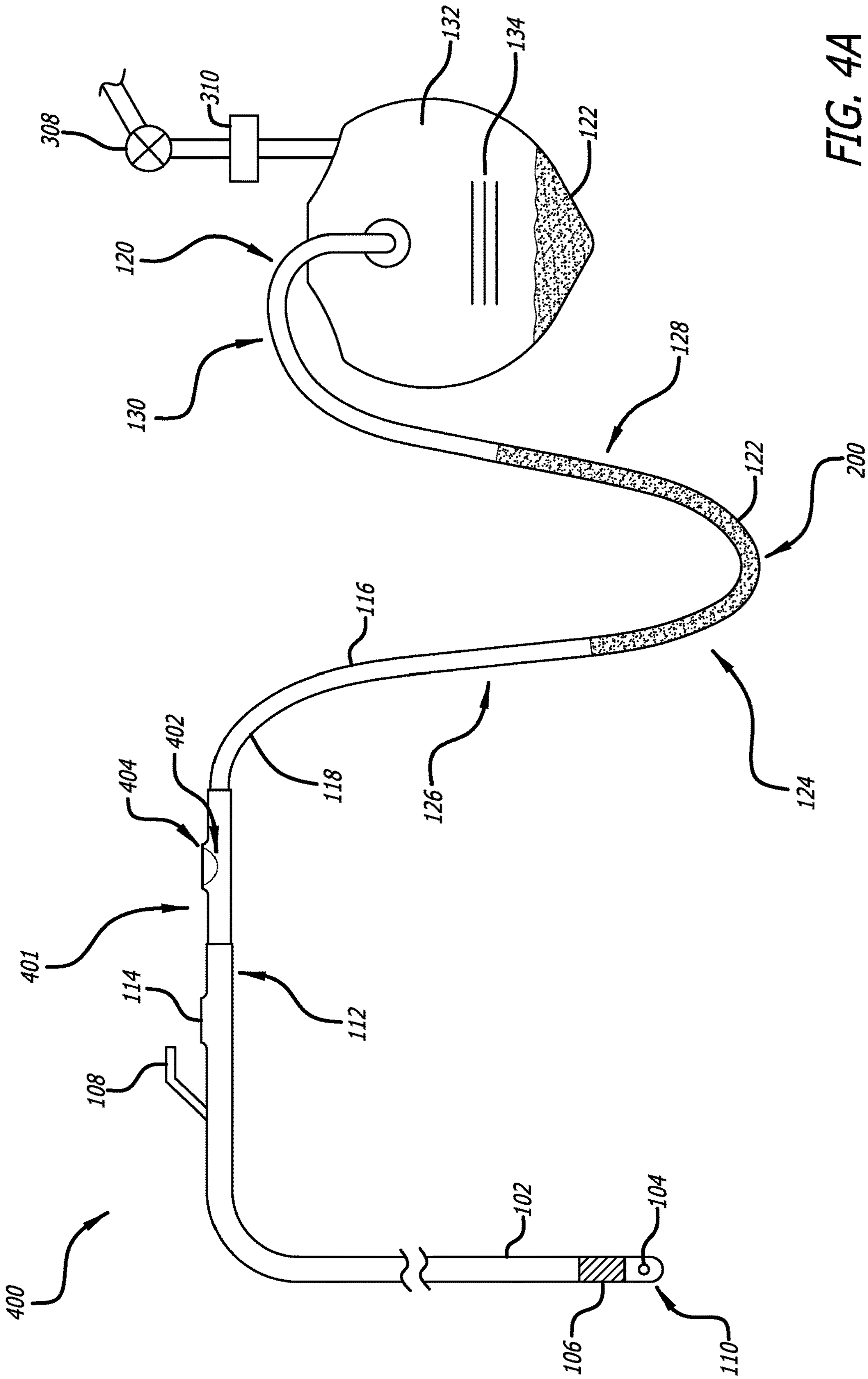
FIG. 4A shows a second catheter and fluid collection system including connection tubing having an occlusion balloon port with an occlusion balloon in a deflated state, in accordance with embodiments disclosed herein.

FIG. 4A shows a second catheter and fluid collection system including connection tubing having an occlusion balloon port with an occlusion balloon in a deflated state, in accordance with embodiments disclosed herein. It will be appreciated that the system illustrated in FIGS. 4A-4B may have analogous features to the systems 100, 300 of FIGS. 1 and 3A-3B. Accordingly, like features are designated with like reference numerals and relevant disclosure set forth above regarding similarly identified features thus may not be repeated hereafter.

The system 400 operates and provides the same functionality as the system 300 of FIGS. 3A-3B. However, instead of having a port and occlusion balloon located within the drainage tubing itself as in the system 300, the system 400 provides connector tubing 401 that includes a balloon occlusion port 404 and an occlusion balloon 402 attached to the port 404 and disposed within the lumen of the connector tubing 401. The port 404 operates in the same manner as the port 304 and the balloon 402 operates in the same manner as the balloon 302. Advantageously, the system 400 allows a clinician to utilize conventional catheters such as the catheter 102 and conventional drainage tubing such as the drainage tubing 116 while still providing the occluding functionality of the system 300.

Figure 4B:
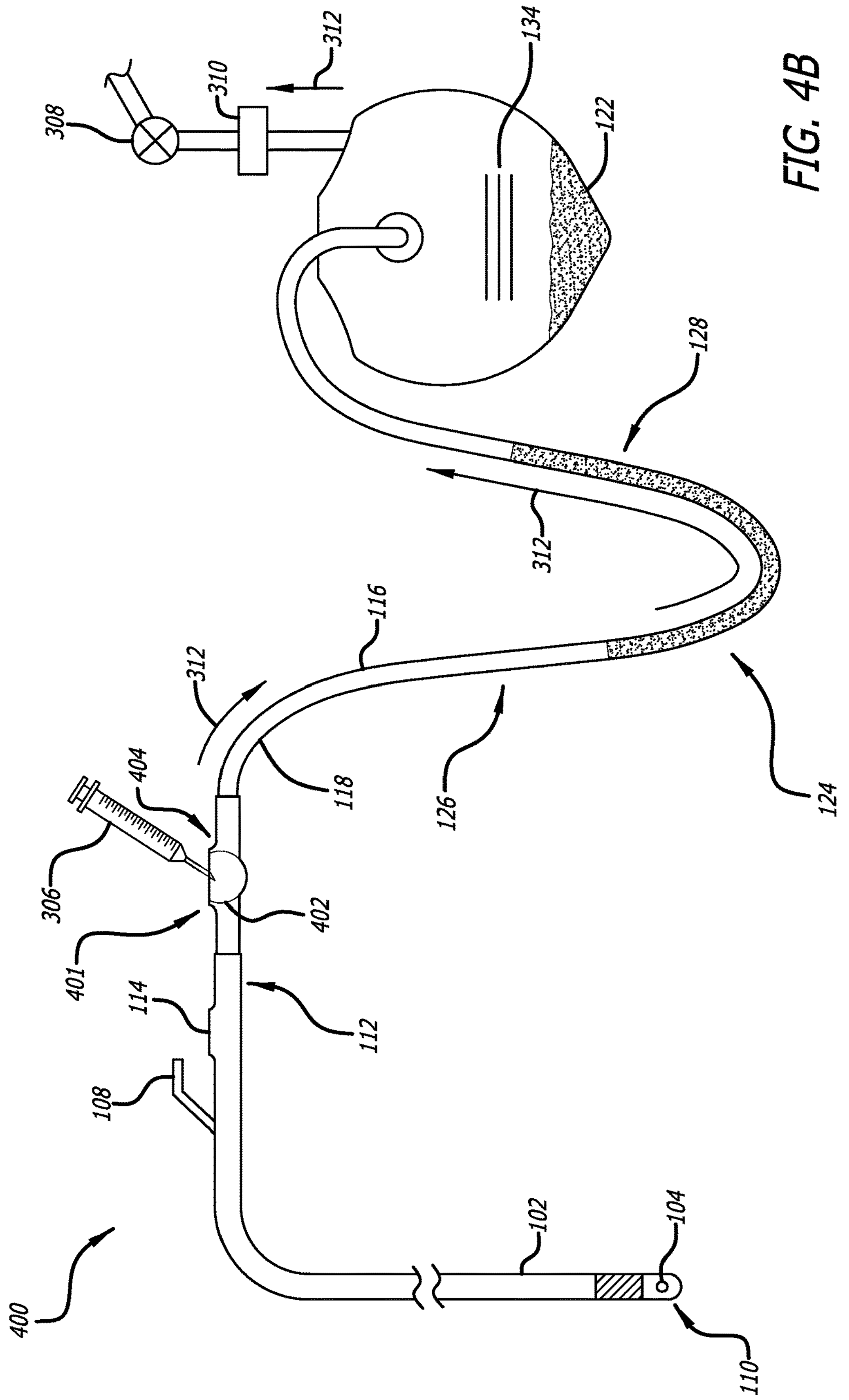
FIG. 4B shows the catheter and fluid collection system of FIG. 4A where the occlusion balloon is in an inflated state, in accordance with embodiments disclosed herein.

FIG. 4B shows the catheter and fluid collection system of FIG. 4A where the occlusion balloon is in an inflated state, in accordance with embodiments disclosed herein. Similar to the discussion above with respect to FIGS. 3A-3C, the needle of the syringe 306 may pierce the membrane of the port 404 such that the needle enters the interior cavity of the balloon 402 enabling the clinician to compress the syringe and inflate the balloon 402.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system for draining a fluid from a patient, the drainage system comprising:
- a catheter;
- a collection container;
- a drainage tube configured to provide fluid communication between the catheter and the collection container, wherein the drainage tube includes a port and a balloon attached to an interior of the drainage tube by surrounding a membrane disposed on an interior side of the port, wherein an interior cavity of the balloon is configured to:
  - receive a gas from a needle that has pierced the port, the needle entering the interior cavity of the balloon, and
  - occlude a lumen of the drainage tube; and
- an output airflow device coupled to the collection container configured to draw airflow out of the drainage tube.

2. The system of claim 1, wherein, when in an inflated state, the balloon occludes the lumen of the drainage tube thereby breaking the fluid communication between the catheter and the collection container and preventing the output airflow device from drawing airflow out of the catheter.

3. The system of claim 1, wherein the membrane is a self-sealing membrane.

4. The system of claim 1, wherein the port is located at a distal end of the drainage tube.

5. The system of claim 1, further comprising a hydrophobic filter coupled in line with the drainage tube between the collection container and the output airflow device.

6. A drainage tube for use within a drainage system for draining a fluid from a patient, the drainage system including a catheter, a collection container and an output airflow device coupled to the collection container, the drainage tube comprising:
- a tubing having a lumen extending from a proximal end to a distal end;
- a port; and
- a balloon attached to an interior of the drainage tube by surrounding a membrane disposed on an interior side of the port, wherein an interior cavity of the balloon is configured to:

receive a gas from a needle that has pierced the port, the needle entering the interior cavity of the balloon, and occlude a lumen of the drainage tube.

7. The drainage tube of claim 6, wherein the drainage tube is configured to provide fluid communication between the catheter and the collection container when the balloon is in a deflated state and terminate the fluid communication when the balloon is in an inflated state thereby preventing the output airflow device from drawing airflow out of the catheter.

8. The drainage tube of claim 6, wherein the membrane is a self-sealing membrane.

9. The drainage tube of claim 6, wherein the port is located at a distal end of the drainage tube.

10. The drainage tube of claim 6, further comprising:

a hydrophobic filter coupled in line with the drainage tube between the collection container and the output airflow device.

11. A drainage system for draining a fluid from a patient, the drainage system comprising:

a catheter;

a collection container;

a drainage tube in fluid communication with the collection container;

an output airflow device coupled to the collection container configured to draw airflow out of the drainage tube; and a connector tube configured to provide fluid communication between the catheter and the drainage tube, wherein the connector tube includes a port and a balloon attached to an interior of the connector tube by surrounding a membrane disposed on an interior side of the port, wherein an interior cavity of the balloon is configured to:

receive a gas from a needle that has pierced the port, the needle entering the interior cavity of the balloon, and occlude a lumen of the connector tube.

12. The system of claim 11, wherein, when in an inflated state, the balloon occludes the lumen of the connector tube thereby breaking the fluid communication between the catheter and the collection container and preventing the output airflow device from drawing airflow out of the catheter.

13. The system of claim 11, wherein the membrane is a self-sealing membrane.

14. The system of claim 11, further comprising a hydrophobic filter coupled in line with the connector tube between the collection container and the output airflow device.

* * * * *